(12) United States Patent
Kim

(10) Patent No.: US 8,728,159 B2
(45) Date of Patent: May 20, 2014

(54) PROSTHETIC BREAST SUPPORT

(75) Inventor: John Y S Kim, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/306,465

(22) Filed: Nov. 29, 2011

(65) Prior Publication Data

US 2012/0143329 A1    Jun. 7, 2012

Related U.S. Application Data

(60) Provisional application No. 61/418,621, filed on Dec. 1, 2010, provisional application No. 61/420,280, filed on Dec. 6, 2010.

(51) Int. Cl.
*A61F 2/12* (2006.01)
(52) U.S. Cl.
CPC ..................... *A61F 2/12* (2013.01)
USPC ........................................ 623/8
(58) Field of Classification Search
CPC ........................................ A61F 2/12
USPC ..................... 623/7, 8; 606/151, 73
See application file for complete search history.

(56) References Cited

U.S. PATENT DOCUMENTS

| 5,705,181 A * | 1/1998 | Cooper et al. ............ 424/426 |
| 6,206,930 B1 * | 3/2001 | Burg et al. ............. 623/23.64 |
| 7,357,810 B2 * | 4/2008 | Koyfman et al. ............ 606/228 |
| 7,476,249 B2 * | 1/2009 | Frank ............................. 623/8 |
| 7,875,074 B2 | 1/2011 | Chen et al. |
| 2009/0082864 A1 * | 3/2009 | Chen et al. ..................... 623/8 |
| 2009/0198333 A1 * | 8/2009 | Becker .......................... 623/8 |
| 2009/0248071 A1 * | 10/2009 | Saint et al. ................ 606/232 |
| 2010/0023029 A1 * | 1/2010 | Young ......................... 606/151 |

OTHER PUBLICATIONS

Arnold et al., The Serratus Anterior Muscle: Intrathoracic and Extrathracic Utilization, 1984, Plastic and Reconstructive Surgery, 73, 240-246.*

* cited by examiner

*Primary Examiner* — Brian Pellegrino
(74) *Attorney, Agent, or Firm* — Klintworth & Rozenblat IP LLC

(57) ABSTRACT

Disclosed is a mammary prosthetic implant with an expandable mammary prosthesis that expands to an enlarged state after implantation. A prosthetic device supports, and conforms to the shape of, the mammary prosthesis before, during, and after the mammary prosthesis is expanding within the implantation site. The prosthetic device has an absorbable main body formed of other than biological tissue, and is penetrable for the in-growth of dermal or subcutaneous tissue. The main body has an anterior end portion, an opposite posterior end portion, and a size relative to the mammary prosthesis upon implantation so that the anterior end portion engages an incised portion of a pectoralis major extending anteriorly of the mammary prosthesis while the opposite posterior end portion engages tissue inferiorly spaced from the incised portion of the pectoralis major and near the inframammary fold. Methods of preparing and using a prosthetic device as described herein also are disclosed.

18 Claims, 5 Drawing Sheets

PROSTHETIC BREAST SUPPORT

RELATED APPLICATION

This application claims the benefit of U.S. Provisional Patent Application No. 61/418,621, filed Dec. 1, 2010, and U.S. Provisional Patent Application No. 61/420,280, filed Dec. 6, 2010, both incorporated herein in their entireties for all purposes.

TECHNICAL FIELD

The subject matter described herein is directed generally to prosthetic implants. In many embodiments, the subject matter is directed towards soft tissue implants, and in some embodiments to non-biological prosthetic devices for supporting an expandable mammary prosthesis. Some embodiments are directed towards methods for preparing or using a prosthetic device, and in other embodiments towards methods for placing or implanting a prosthetic device.

BACKGROUND

Allografts known as acellular dermal matrices, or dermices, are used in the field of soft-tissue replacement. In breast reconstruction, an acellular dermis acts as a sling to support tissue expanders or implants. This acellular dermis improves inframammary fold definition, implant coverage (for example sufficient skin tissue thickness so that the implant cannot be discerned), and aesthetic appearance.

Acellular dermis is known to have different forms, which include a fully hydrated human-derived form, a freeze-dried or solvent-dried human-derived form, and a porcine-derived form. Commercial examples include FLEXHD®, a fully-hydrated human-derived dermis presently available from Ethicon; ALLODERM®, NEOFORM®, and DERMAMATRIX®, which are dehydrated human derived products available from LifeCell Corp., Tutogen Medical, Inc., and Synthes CMF respectively; and PERMACOL® and STRATTICE®, porcine-derived products available from Coviden Surgical and LifeCell Corp. respectively.

In light of their allogeneic or xenogeneic nature, these known acellular dermis products may transmit disease from the host, thereby causing complications such as inflammatory reactions. Additionally, the acellular dermis products must be sterile, and the specialized processes to produce the sterilized products are known to have errors that permit contamination. Also, these biologically based acellular dermis are very expensive due to the costs for harvesting, sterilizing, and storing the tissue. Newer products that utilize alternative sources of dermis are known, but still have price points comparable to human dermis.

SUMMARY

It has now been found that a mammary prosthetic implant can use a prosthetic device to provide support for an expandable mammary prosthesis that is configured to expand to an enlarged state after implantation. The prosthetic device for supporting the mammary prosthesis conforms to the shape of the mammary prosthesis before, during, and after the mammary prosthesis is expanding within the implantation site. The prosthetic device fashions an absorbable main body formed of other than biological tissue, and is penetrable for the in-growth of dermal or subcutaneous tissue. For many of the embodiments, the main body comprises an anterior end portion and an opposite posterior end portion. The main body may have a size relative to the mammary prosthesis upon implantation so that the anterior end portion engages an incised portion of a pectoralis major extending anteriorly of the mammary prosthesis while the opposite posterior end portion engages tissue inferiorly spaced from the incised portion of the pectoralis major and near the inframammary fold.

In many embodiments, a prosthetic device (also referred to as a sling or support) prepared in accordance with the present teachings can be made less expensively than can human- or porcine-derived supports, and can be made of materials that are not allogeneic or xenogeneic and that thereby mitigate the risk of disease transmission from the host.

The subject matter herein provides a method for implanting a prosthetic device for supporting a mammary prosthesis. In some embodiments, this generally includes placing a prosthetic device along a generally inferior side of the mammary prosthesis. Here to, the prosthetic device may have an absorbable main body formed of other than biological tissue and being penetrable by the in-growth of dermal or subcutaneous tissue. The method of these embodiments include engaging an anterior end portion of the prosthetic device to an incised portion of a pectoralis major extending anteriorly of the implanted mammary prosthesis. The method also may include engaging an opposite posterior end portion of the prosthetic device to tissue near the inframammary fold and inferiorly relative to the position of the anterior end portion. The prosthetic device is of a size to support the mammary prosthesis when the anterior and posterior ends are so engaged.

In other embodiments, the subject matter herein provides a method for placing a prosthetic device for supporting an expandable mammary prosthesis. Generally, the method here includes sizing the prosthetic device where the prosthetic device is formed of an absorbable mesh formed of polydioxanone. Sizing the prosthetic device may include measuring the distance from a first location at an incised portion of a pectoralis major extending anteriorly of the implanted expandable mammary prosthesis to a second location at tissue inferior to the first location and near the inframammary fold. The sizing step may include providing the mesh in a form that extends approximately from the first location to the second location. Also, the method includes securing the mesh to the first and second locations, and placing the mesh against a generally inferior side of the expandable mammary prosthesis to conform the mesh to the shape of the expandable mammary prosthesis.

DESCRIPTION

In a human breast reconstruction after a mastectomy, two surgical phases are often used. In the first phase, an expandable mammary prosthesis (or simply expander) is implanted and filled with fluid to expand over time in order to stretch the overlying skin layers (epideral, dermis, and subcutaneous). In the second phase, the expander is replaced with a softer permanent mammary prosthesis. To limit damage to the skin layers and provide them better support, the expander and implant are placed underneath (posteriorly) to the pectoralis major. The pectoralis major, however, has a tendency to hold the implant in an unnatural superior and/or lateral position, and is therefore incised to release the implant to extend lower (inferiorly) to a more natural position. The prosthetic device described herein is placed inferiorly to the expander during at least the first phase of the reconstruction to act as a sling for the expander and to bridge the gap between the incised pectoralis major extending on the anterior side of the expander and more posterior and inferior tissue near the inframammary fold.

Figure 1:
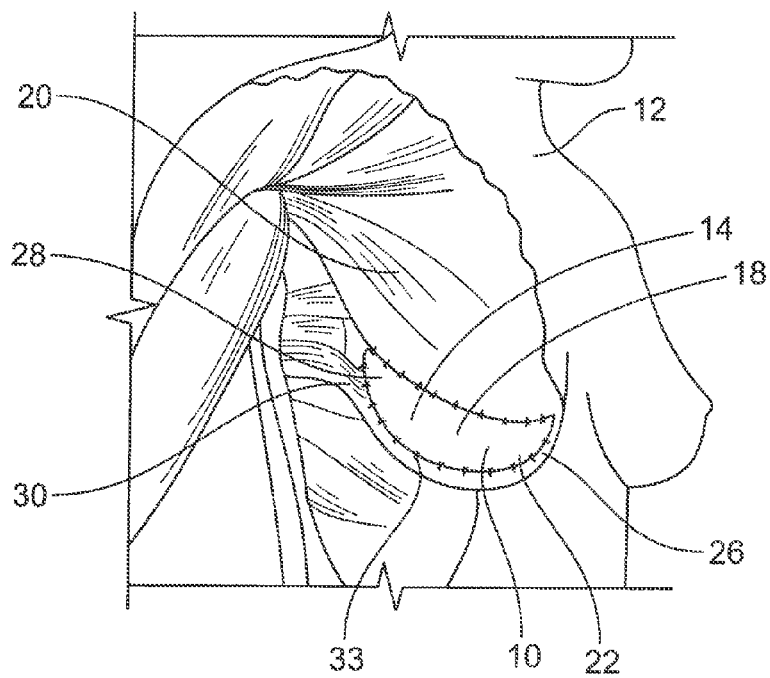
FIG. 1 is a front and side perspective view of an implanted prosthetic device at a breast reconstruction surgical site and shown with the surrounding skin removed to reveal underlying muscle.
Figure 2:
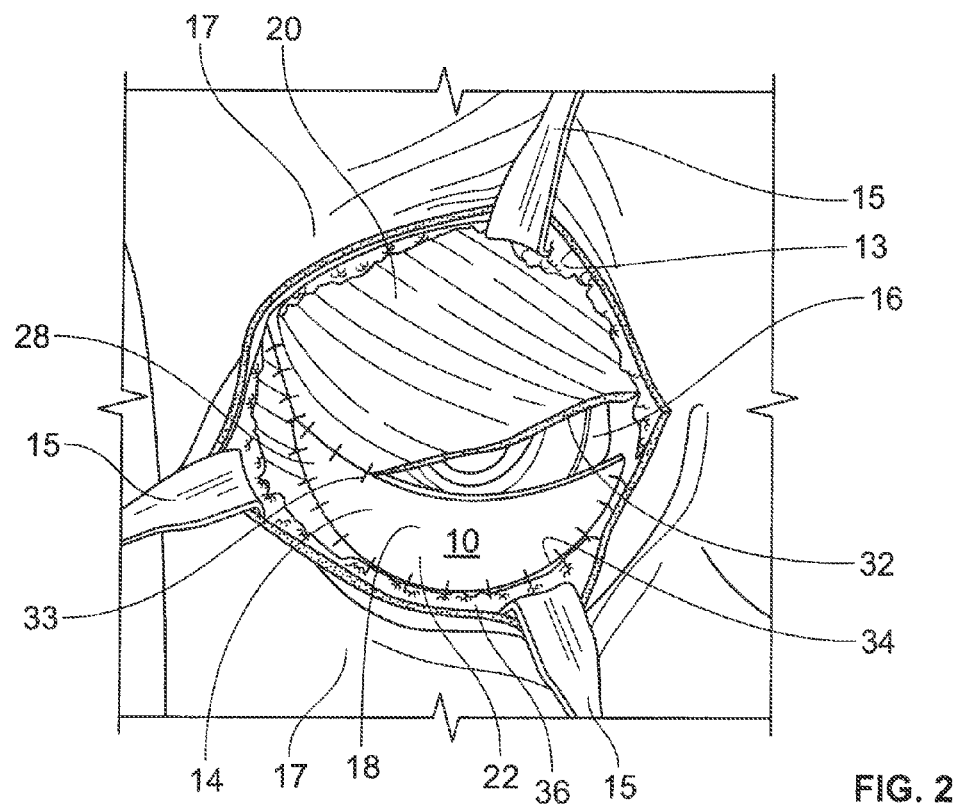
FIG. 2 is a front elevation of the implanted prosthetic device of FIG. 1 with the skin tissues retracted and the prosthetic device partially secured.
Figure 3:
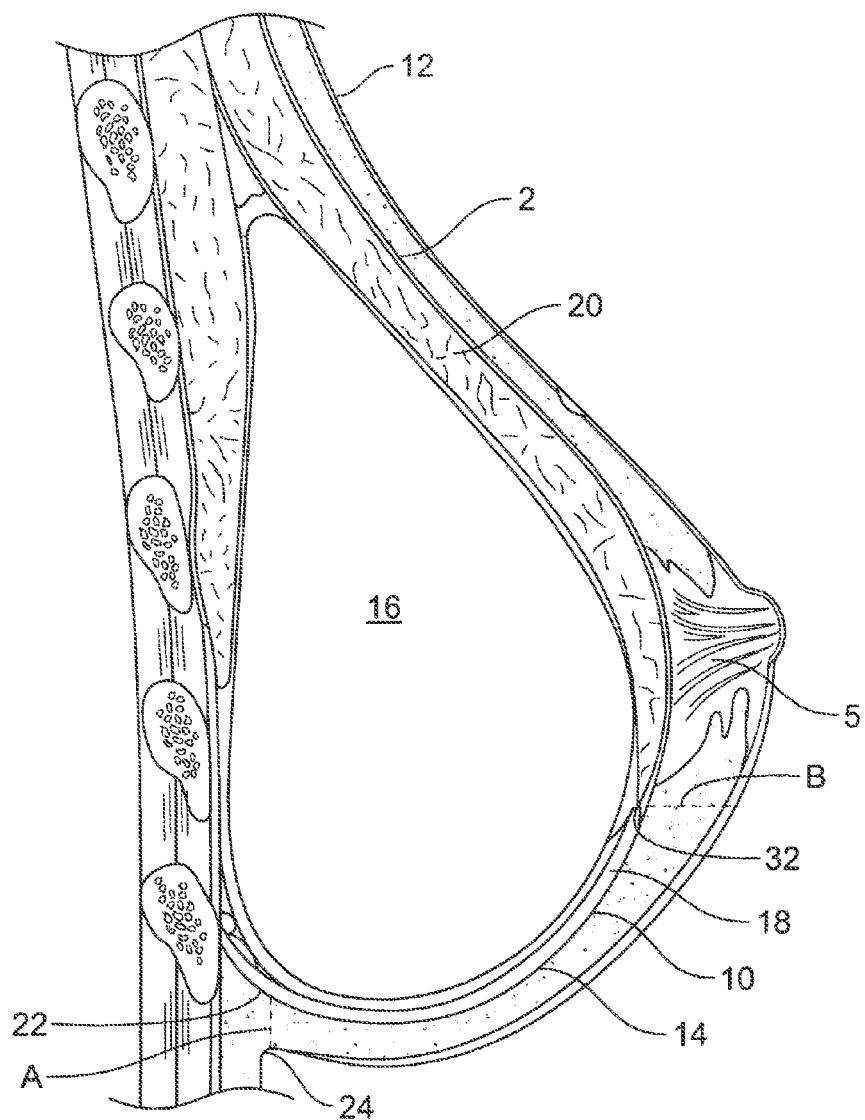
FIG. 3 is a side cross-sectional view of the implanted prosthetic device of FIG. 1.

Referring to FIGS. 1-3, the prosthetic device 10 is shown implanted on a person 12 at a mammary surgical site 13 (FIG. 2) shown with retractors 15 holding back the mammary skin flap (or mastectomy flap) 17. The prosthetic device 10 includes a generally flat, absorbable main body 14 to support a mammary prosthesis 16. The mammary prosthesis 16 may be conventional and in one form is expandable by filling it with fluids. The main body 14 also has an anterior end portion 18 that engages, or is affixed, superiorly to a portion of an incised pectoralis major 20 extending anteriorly of the mammary prosthesis 16. In one form, the anterior end portion 18 is fixed near or to the incised edge 32 of the anteriorly extending pectoralis major 20.

A posterior end portion 22 of the main body 14 engages tissue near the inframammary fold 24 (FIG. 3) and, in most cases, inferiorly spaced from the incised pectoralis major 20. Specifically, the posterior end portion 22 may be affixed to the chest wall, the rectus fascia, and/or the surrounding soft tissue such as the mastectomy skin flap 17 to inferiorly secure the main body 14. It will be appreciated that the incision through the skin tissue defining the surgical site also defines the edges of the mastectomy skin flap 17. Thus, when the incision is located along the inframammary fold as shown by incision A on FIG. 3, then the posterior end portion 22 may be attached to, or near, the dermal and/or subcutaneous tissue forming the inferior edge 34 of the opening 36 to the surgical site 13. If, however, the incision through the skin tissue is more superior along the breast (for example, at or near nipple height as shown by incision B on FIG. 3), in this case the posterior end portion 22 may be attached to, or near, the base of the inferior mastectomy skin flap. In either case, in one form, the posterior end portion 22 may be attached near the inframammary fold 24.

Alternatively or additionally, the posterior end portion 22 may be secured to an inferior, remainder section 26 of the pectoralis major (FIG. 1) separated from its anterior portion 20. Such an inferior section 26 may not be present when the entire pectoralis major is placed over the mammary prosthesis 16.

The lateral end portion 28 of the main body 14 may be fixed to the serratus anterior 30. The main body 14 may be fixed to the muscular or skin tissue by sutures 33 (as shown in FIGS. 1-2) or other suitable fasteners such as clips, tabs, staples, or adhesives, which in one form may be absorbable. With this configuration, the prosthetic device 10 forms an inferiorly positioned pocket to receive the expandable mammary prosthesis 16 and to act as a sling or a bridge to support the expandable mammary prosthesis 16. By another approach, either additionally or alternatively (without any suture fixation for example), the prosthetic device 10 is fixed directly to the expandable mammary prosthesis 16 by an adhesive or other fastener. No matter how the prosthetic device 10 is fixed within the mastectomy site 13, the prosthetic device 10 may be formed of a material described below that expands or stretches to conform to the shape of the expandable mammary prosthesis 16 whether before, during, or after the expandable mammary prosthesis 16 is expanded within the implantation site (including, in other words, while the implantation site is closed) to hold the mammary prosthesis 16. Thus, it will be understood that in one form, the mammary prosthesis 16 may be in a certain initial state, whether inflated or not, to be initially maintained when the surgical site is closed, and that it is this initial shape that the prosthetic device 10 may first conform to before the mammary prosthesis is expanded in situ.

Referring to FIG. 3, the main body 14 is configured so that the anterior end portion 18 extends higher (superiorly) relative to the posterior end portion 20 that is fixed near the inframammary fold 24. Thus, in one alternative form, the prosthetic device 10 is formed of a single sheet or generally flat body without a substantial back wall. For example, in cross-section, the main body 14 is J-shaped rather than U-shaped.

The prosthetic device 10 may have any suitable dimensions, and generally should be sized to support the mammary prosthesis 16 adequately while bridging the muscular gap between the incised pectoralis major 20 and the inferior portion of the mammary skin flap 17 (whether the free end or base of the flap depending on the location of the incision as explained above). In some embodiments, it is contemplated that a surgeon may cut the main body 14 to a length that extends approximately from the pectoralis major to the tissue near the inframammary fold 24 where the posterior end portion 22 is to be affixed to muscular or other soft tissue. This may be accomplished by first measuring the distance between these two points and then cutting the main body 14 to a length that approximately matches the length between the two points before implanting the prosthetic device 10. Alternatively, the main body 14 may be placed first in position over the mammary prosthesis 16 and from the pectoralis major 20 to the tissue near the inframammary fold 24 to then cut the main body 14 to the correct length in situ. In other forms though, the surgeon may select a prosthetic device that has a predetermined length that approximately matches the length between the two points described above, especially when the prosthetic device is supplied in different sizes. In this case, the main body 14 is provided in pre-cut lengths or otherwise prefashioned to the appropriate size. Thus, references to "sized" and "of a size" and like terms without more detail are not intended to be limited to a step of cutting or fashioning a device to size or a certain way of cutting the device, but rather refer to the dimensions of the device irrespective of whether or how the device is cut (whether or not cut in situ for example). In one form, the material for the main body is provided in large sheets for the surgeon to cut to a desired size. In other forms, the main body 14 may be provided in rectangular sheets 4 to 8 cm wide and 14 to 18 cm long, and in one specific form, 6 cm by 16 cm. In other forms, the main body may be provided in other shapes such as a generally semicircle or crescent shape for example. The main body 14 likewise may be of any suitable thickness, for instance, a thickness of approximately 0.1 to 10 mm thick, and in one form, approximately 0.5 to 1.0 mm thick.

In one aspect, the main body 14 may be at least partially, or substantially, formed of a material that is absorbable and that is at least partially, or substantially or completely, formed of other than biological tissue. Terms such as "other than biological" or "non-biologic" are intended to connote a body that is more than 50%, and in some embodiments more than 95%, composed of a material that is not immediately derived from a biological source. The material that forms the body should be penetrable by the in-growth of dermal or subcutaneous tissue to hasten the fusing of the main body 14 to the surrounding tissue and the eventual absorption process of the main body 14. The material may be an absorbable or biodegradable polymer. The material may also be a monofilament or other suture material. The material also may be selected such that the body is easy to trim or shape to better fit the shape of the gap between the pectoralis major 20 and the inferior portion of the mammary flap 17. However, it is not necessary to trim the material because the trim or extra material will be absorbed anyway by the recipient.

One suitable material is polydioxanone (also referred to as PDO, PDS, or poly-p-dioxanone). Such a polydioxanone prosthetic device may last at least 10-12 weeks before significant break down, can feel soft, and may be slightly distensible. In other words, this material also expands sufficiently to provide support while the expandable mammary prosthesis 16 expands and is enlarged outwardly (anteriorly). In addition to expansion of the prosthetic device 10 in the posterior-anterior direction, the expansion may also occur in the lateral-medial direction.

Other absorbable materials that may be used are based on polylactic acid (PLA), polyglycolic acid (PGA), or poly e-caprolactone (PCL), or mixtures or co-polymers thereof including poly(glycolide-co-caprolactone) (PGA/PCL), poly(D,L-lactide-co-caprolactone) (PLA/PCL), poly(D, L-lactide-co-glycolide) (PLA/PGA), poly(glycolide-co-trimethylene carbonate) (PGA/PTMC) such as, poly(L-lactide-co-glycolide) (PLLA/PGA), poly(L-lactide-co-glycolide) (PLLA/PGA), poly(L-lactide-co-D, L-lactide) (PLLA/PLA). Some specific examples of these include Polycaprolate (DEXON™ II), Polyglactin 910 (VICRYL™), Poliglecaprone 25 (MONOCRYL™), POLYSORB™, polyglyconate (MAXON™), and synthetic polyester composed of glycolide, caprolactone, trimethylene carbonate, and lactide (CAPROSYN™).

Other suitable materials include polyethylene oxide (PEO), polypropylene fumarate, poly(ethyl glutamate-co-glutamic acid), poly(tert-butyloxy-carbonylmethyl glutamate), polycaprolactone co-butylacrylate, polyhydroxybutyrate (PHBT) and copolymers of polyhydroxybutyrate, poly(phosphazene), poly(phosphate ester), poly (amino acid) and poly(hydroxy butyrate), maleic anhydride copolymers, polyphosphazenes, polyiminocarbonates, poly [(97.5 dimethyl-trimethylene carbonate)-co-(2.5% trimethylene carbonate)], cyanoacrylate, and polyethylene oxide.

Figure 4:
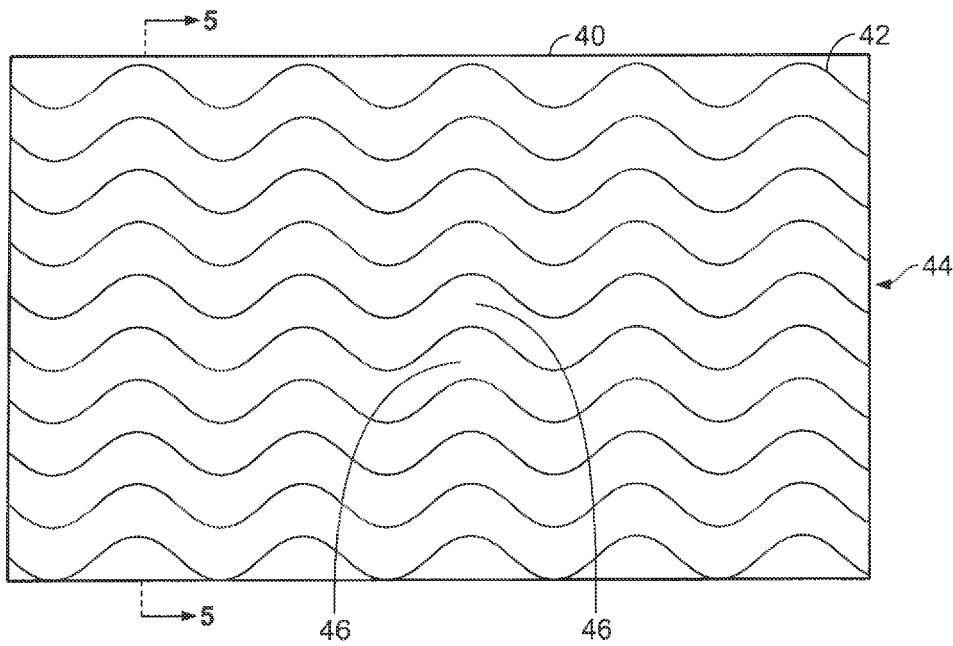
FIG. 4 is a plan view of one embodiment of a patterned prosthetic device, the device of this embodiment having protrusions.
Figure 5:
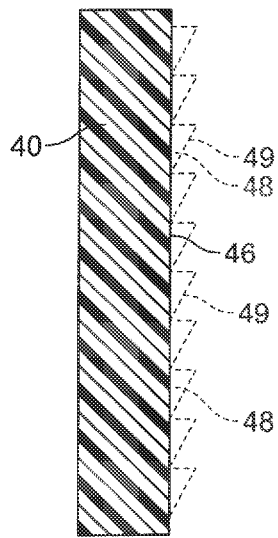
FIG. 5 is a cross-sectional view of the embodiment of FIG. 4 taken along line 5-5.

Referring now to FIG. 4, an alternative main body 40 may have a generally solid form where pores for the in-growth of surrounding tissue are very small. In this illustrated form, the main body 40 has filaments 42 that are arranged in specific patterns, here a curving or undulating line pattern 44 as one example pattern. The illustrated main body 40 has an exterior surface 46 that is substantially initially flat. In a modified example form, single spaced filaments or spaced groups of filaments 48 may form a protrusion 49 (shown in dashed line on FIG. 5) extending outwardly from a base formed at the location where the exterior surface 46 would have been (or in other words, a three-dimensional protrusion). The protrusions 49 may be on the superior surface, the interior surface, or both to form a rough surface for better anchoring of the main body 40 to the expander 16 and/or the surrounding tissue. The rough surface on the inferior side also promotes tissue growth onto the main body 14.

Figure 7:
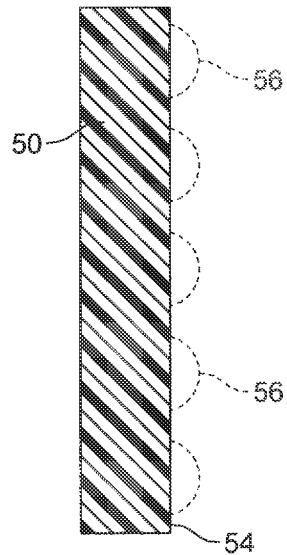
FIG. 7 is a cross-sectional view of the prosthetic device of FIG. 6 taken along line 7-7.
Figure 6:
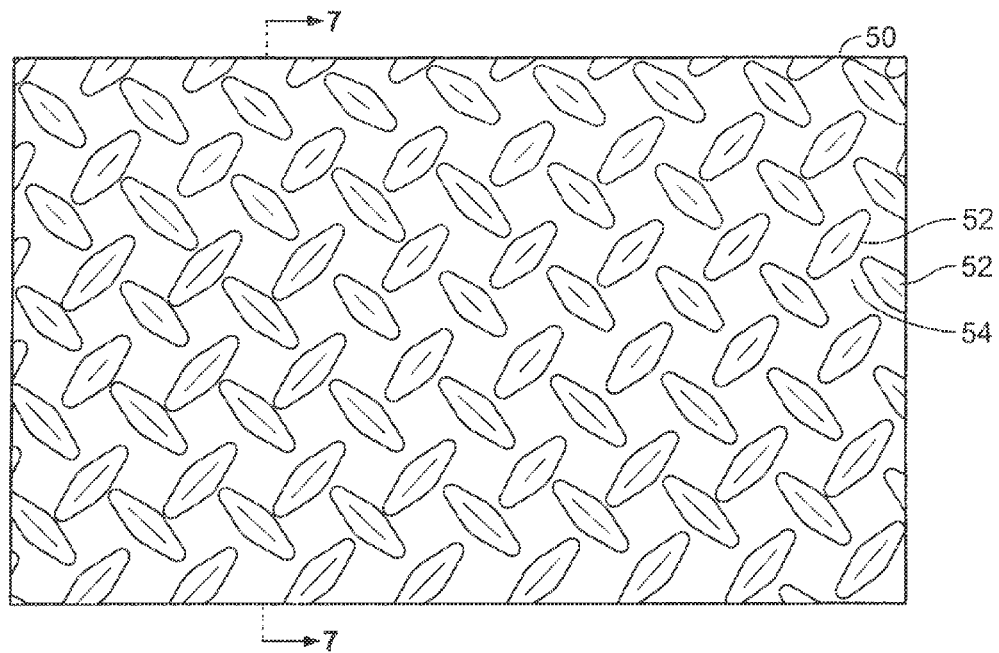
FIG. 6 is a plan view of an alternative patterned prosthetic device.

Referring to FIG. 6, as with the previously depicted main body 40, the illustrated main body 50 has a crossing pattern of filaments 52 in a diamond shape. The main body 50 may have a substantially flat exterior surface 54. Otherwise, the main body 50 may have protrusions 56 (shown in dashed line on FIG. 7) extending outwardly from a base formed at the location of the exterior surface 54. Many other patterns are possible where filaments cross each other, extend in non-parallel directions, remain parallel, remain straight, and/or are curved.

Figure 8:
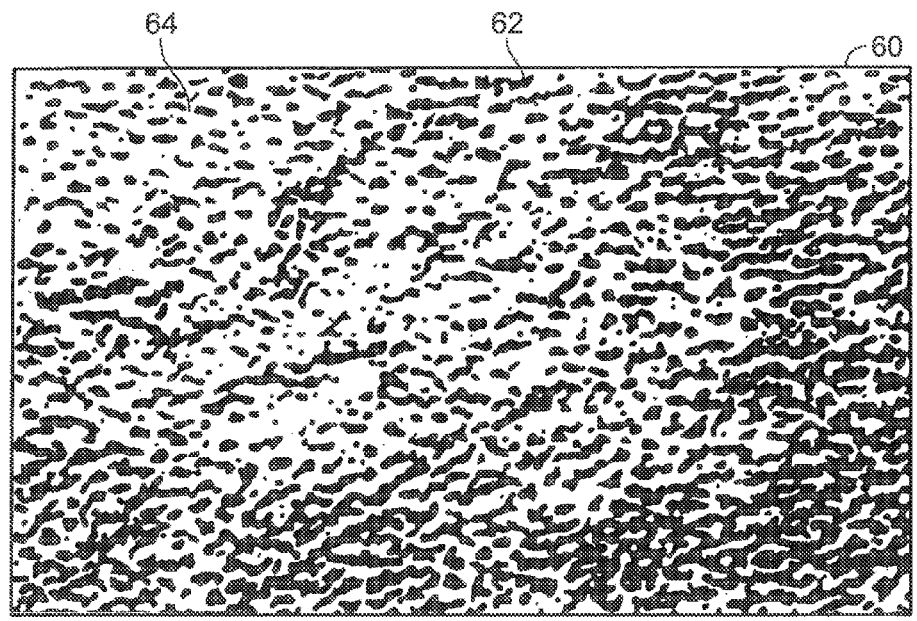
FIG. 8 is a plan view of a textured prosthetic device.

Referring to FIG. 8, a textured main body 60 is provided where the filaments 62 are placed randomly within the main body 60 to form a rough exterior surface 64. The density and placement of the filaments may be controlled to form one area on the main body rougher than another area on the exterior surface 64.

Figure 9:
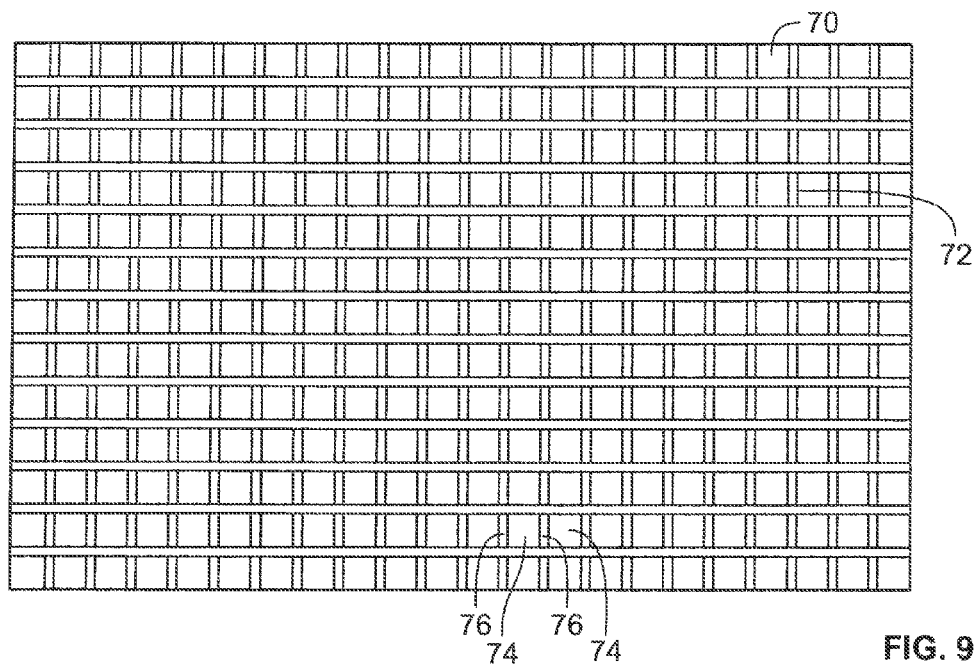
FIG. 9 is a plan view of a mesh-configured prosthetic device.

Referring to FIG. 9, a main body 70 has a mesh or net 72 with interspersed gaps or spaces 74 formed by filaments 76. In one form, the spaces 74 are wider than the width of the filament or filaments 76 between adjacent spaces 74. The mesh 72 may be formed from a single piece of material (such as in a mold), may be woven filaments, or simply may have one layer of filaments extending in one direction and another layer extending in another direction as shown in FIG. 9.

Figure 10:
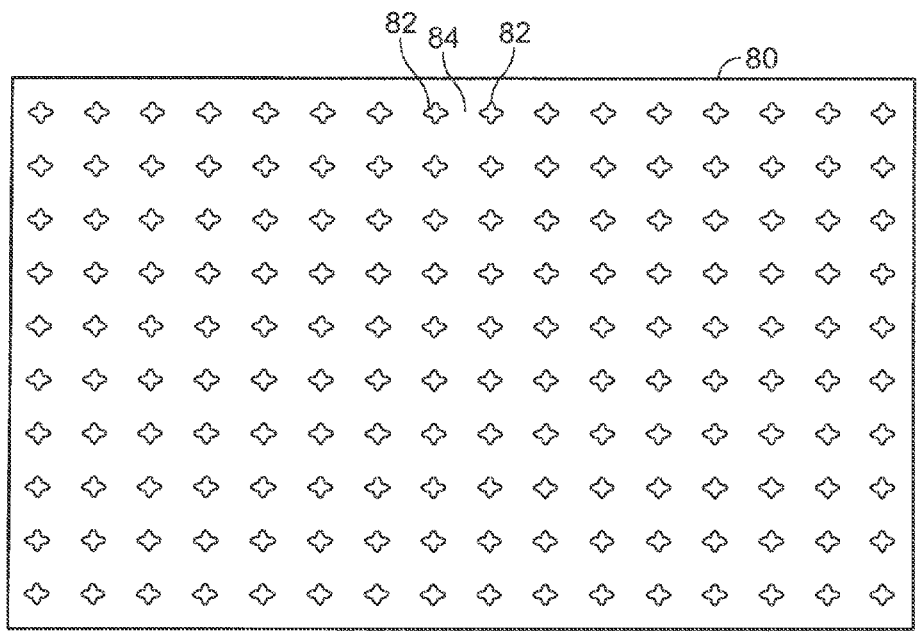
FIG. 10 is a plan view of a lattice-configured prosthetic device.

Referring to FIG. 10, in yet another example with interspersed gaps, a lattice main body 80 is more solid than a mesh and has spaced apertures 82 that may be smaller than the width of the filament or filaments 84 forming the distance between adjacent apertures 82.

For any of the main bodies 40, 50, 60, 70, and 80, the spaces or apertures may have many shapes other than those depicted. For instance, the spaces or apertures may be lobed or have a plus-sign shape, or may have a different symmetric shape, or may have other non-symmetric or non-regular shapes.

The main body 14 may also be coated or impregnated with various functional materials. For example, the main body may have a coating or filling whose function is to inhibit bacterial growth or to promote healthy soft tissue growth. These coating or fillers may include antibiotics, collagen, hyaluronic acid, growth factors, cytokines, and many others.

A prosthetic device as describe herein has a reduced risk of disease transmission from donors and reduced risk of inflammatory reactions relative to the heretofore-described human- and porcine-derived devices. The device likewise has increased sterility, and in many embodiments cost efficiency compared with the heretofore-described products. Additionally, the device maintains the benefits of the known products, including suitable inframammary fold definition, implant coverage, and aesthetic appearance.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description or connotation of certain embodiments as "preferred" embodiments, and other recitation of embodiments, features, or ranges as being preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service

What is claimed is:

1. A mammary prosthetic implant, comprising:
   an expandable mammary prosthesis that is configured to expand to an enlarged state after implantation; and
   a prosthetic device for supporting the expandable mammary prosthesis and conforming to the shape of the expandable mammary prosthesis before, during, and after the expandable mammary prosthesis is expanding within the implantation site,
   the prosthetic device having an absorbable main body formed of other than biological tissue, being penetrable for the in-growth of dermal or subcutaneous tissue,
   the absorbable main body comprising an anterior end portion and an opposite posterior end portion,
   the absorbable main body selected from the group consisting of filaments arranged in a diamond shape, filaments arranged in a curving or undulating pattern, and spaced apertures which are lobed or have a plus-sign shape,
   the absorbable main body made of a material comprising polydioxanone and having a pre-determined, pre-cut, or cut size relative to the expandable mammary prosthesis upon implantation so that the anterior end portion engages an incised portion of a pectoralis major extending anteriorly of the expandable mammary prosthesis while the opposite posterior end portion engages tissue inferiorly spaced from the incised portion of the pectoralis major and at an inframammary fold.

2. The mammary prosthetic implant of claim 1 wherein the anterior end portion has a pre-determined, pre-cut, or cut size for affixing the anterior end portion to the incised portion of the pectoralis major.

3. The mammary prosthetic implant of claim 1 wherein the posterior end portion has a pre-determined, pre-cut, or cut size for affixing to at least one of:
   the chest wall,
   the mastectomy flap,
   the rectus fascia, or
   an inferior portion of the pectoralis major separated from the incised portion of the pectoralis major.

4. The mammary prosthetic implant of claim 1 wherein the absorbable main body has a lateral end portion and a pre-determined, pre-cut, or cut size for affixing the lateral end portion to a serratus anterior.

5. The mammary prosthetic implant of claim 1 wherein at least one of the anterior or posterior end portions is affixed to the expandable mammary prosthesis.

6. The mammary prosthetic implant of claim 1 wherein the absorbable main body is formed at least partially of a monofilament material.

7. The mammary prosthetic implant of claim 1 wherein the absorbable main body is formed of an absorbable polymer.

8. The mammary prosthetic implant of claim 1 wherein the absorbable main body is formed of a material based on of at least one of:
   polylactic acid (PLA),
   polyglycolic acid (PGA), or
   poly e-caprolactone (PCL).

9. The mammary prosthetic implant of claim 1 wherein the absorbable main body comprises:
   a lattice.

10. The mammary prosthetic implant of claim 1 wherein the absorbable main body comprises:
    a textured surface formed by filaments in a random arrangement.

11. The mammary prosthetic implant of claim 1 wherein the absorbable main body comprises:
    a flat exterior surface and protrusions that extend outwardly from the exterior surface.

12. The mammary prosthetic implant of claim 1 wherein the absorbable main body is coated or impregnated with at least one of:
    an antibiotic,
    collagen,
    a growth factor,
    a cytokine, or
    hyaluronic acid.

13. The mammary prosthetic implant of claim 1 wherein the prosthetic device is a single sheet that is semicircular or crescent shaped.

14. The mammary prosthetic implant of claim 1 wherein a pre-determined, pre-cut, or cut first length of the absorbable main body matches a second length extending between the pectoralis major and the inframammary fold.

15. The mammary prosthetic implant of claim 1 wherein the absorbable main body is made of a material comprising more than fifty percent (50%) polydioxanone.

16. The mammary prosthetic implant of claim 15 wherein the absorbable main body is completely formed of the other than biological tissue, the other than biological tissue comprising more than fifty percent (50%) of the polydioxanone.

17. The mammary prosthetic implant of claim 15 wherein the absorbable main body is completely formed of the other than biological tissue, the other than biological tissue comprising more than ninety-five percent (95%) of the polydioxanone.

18. The mammary prosthetic implant of claim 1 wherein the absorbable main body is coated or impregnated with an antibiotic or a cytokine.

* * * * *